US007662178B2

(12) United States Patent
Marx et al.

(10) Patent No.: US 7,662,178 B2
(45) Date of Patent: Feb. 16, 2010

(54) C3 EXOENZYME-COATED STENTS AND USES THEREOF FOR TREATING AND PREVENTING RESTENOSIS

(75) Inventors: Steven O. Marx, New York, NY (US); Andrew R. Marks, Larchmont, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 87 days.

(21) Appl. No.: 12/150,695

(22) Filed: Apr. 29, 2008

(65) Prior Publication Data

US 2008/0208326 A1 Aug. 28, 2008

Related U.S. Application Data

(63) Continuation of application No. 10/326,936, filed on Dec. 20, 2002, now Pat. No. 7,364,586.

(60) Provisional application No. 60/343,030, filed on Dec. 21, 2001.

(51) Int. Cl.
*A61F 2/82* (2006.01)
*A61F 2/00* (2006.01)

(52) U.S. Cl. .................................... 623/1.42; 623/1.43

(58) Field of Classification Search ................ 623/1.15, 623/1.16, 1.17, 1.19, 1.2, 1.21, 1.22, 1.42, 623/1.43, 1.44, 1.45, 1.46, 1.47, 1.48, 1.49; 427/2.24, 2.25, 456

See application file for complete search history.

(56) References Cited

U.S. PATENT DOCUMENTS

| | | | |
|---|---|---|---|
| 5,163,952 | A | 11/1992 | Froix |
| 5,304,121 | A | 4/1994 | Sahatjian |
| 5,804,604 | A | 9/1998 | Frankel |
| 5,851,786 | A | 12/1998 | Johnson |
| 6,153,252 | A | 11/2000 | Hossainy et al. |
| 6,179,817 | B1 | 1/2001 | Zhong et al. |
| 6,306,166 | B1 | 10/2001 | Barry et al. |

(Continued)

FOREIGN PATENT DOCUMENTS

JP 2002-193838 7/2002

(Continued)

OTHER PUBLICATIONS

Barth, H., Hofmann, F., Olenik, C., Just, I. and Aktories, K. (1998) The N-terminal part of the enzyme component (C2I) of the binary *Clostridium botulinum* C2 toxin interacts with the binding component C2II and functions as a carrier system for a Rho ADP-ribosylating C3-like fusion toxin. Infect. Immun. 66: 1364-1369.

(Continued)

*Primary Examiner*—Thomas J Sweet
(74) *Attorney, Agent, or Firm*—John P. White; Cooper & Dunham LLP

(57) ABSTRACT

This invention provides a stent for implantation in a blood vessel or other tissue, wherein the stent is coated with or contains C3 exoenzyme, a chimeric version thereof or an inhibitor of RhoA. This invention also provides a method for treating or inhibiting the onset of restenosis in a subject which comprises implanting one of the instant stents in the subject's blood vessel.

64 Claims, 1 Drawing Sheet

U.S. PATENT DOCUMENTS

| | | | |
|---|---|---|---|
| 6,306,423 | B1 | 10/2001 | Donovan et al. |
| 6,306,993 | B1 | 10/2001 | Rothbard et al. |
| 6,316,003 | B1 | 11/2001 | Frankel |
| 6,344,035 | B1 | 2/2002 | Chudzik et al. |
| 6,358,556 | B1 | 3/2002 | Ding et al. |
| 6,379,382 | B1 | 4/2002 | Yang |
| 6,387,124 | B1 | 5/2002 | Buscemi et al. |
| 6,391,052 | B2 | 5/2002 | Buirge et al. |
| 6,495,663 | B1 | 12/2002 | Rothbard et al. |
| 6,558,733 | B1 | 5/2003 | Hossainy et al. |
| 6,579,847 | B1 | 6/2003 | Unger |
| 6,767,544 | B2 | 7/2004 | Brooks et al. |
| 6,776,991 | B2 | 8/2004 | Naumann |
| 6,958,147 | B1 | 10/2005 | Alitalo et al. |
| 2002/0041898 | A1 | 4/2002 | Unger et al. |
| 2003/0077310 | A1 | 4/2003 | Pathak et al. |
| 2003/0130722 | A1 | 7/2003 | Marx et al. |

FOREIGN PATENT DOCUMENTS

WO WO 03/059192 7/2003

OTHER PUBLICATIONS

Boquet, P., Popoff, M.R., Giry, M., Lemichez, E. and Bergez-Aullo, P. (1995) Inhibition of p21 Rho in intact cells by C3 diptheria toxin chimera proteins. Methods Enzymol. 256: 297-306.

Brugidou, J., Legrand, C., Mery, J. and Rabie, A. (1995) The retro-inverso form of a homeobox-derived short peptide is rapidly internalised by cultured neurones: a new basis for an efficient intracellular delivery system. Biochem. Biophys. Res. Comm. 214(2): 685-693.

Cao, W., Mohacsi, P., Shorthouse, R., Pratt, R., and Morris, R. (1995) Effects of rapamycin on growth factor-stimulated vascular smooth muscle cell DNA synthesis:inhibition of basic fibroblast growth factor and platelet-derived growth factor action and antagonism of rapamycin by FK506. Transplantation 59: 390-395.

Dillon, S.T., and Feig, L.A. (1995) Purification and assay of recombinant C3 transferase. Methods in Enzymology 256: 174-184.

Gallo, R., Padurean, A., Jayaraman, T., Marx, S.O., Roque, M., Adelman, S., Chesebro, J., Fallon, J., Fuster, V., Marks, A.R., and Badimon, J.J. (1999) Inhibition of intimal thickening after balloon angioplasty in porcine coronary arteries by targeting regulators of the cell cycle. Circulation 99: 2164-2170.

Gregory, C., Huie, P., Billingham, M., and Morris, R. (1993) Rapamycin inhibits arterial intimal thickening caused by both alloimmune and mechanical injury. Transplantation 55: 1409-1418.

Kato, J.M., Matsuoka, M., Polyak, K., Massaque, J., and Sherr, C.J. (1994) Cyclic AMP-induced G1 phase arrest mediated by an inhibitor ($p27^{kipl}$) of cyclin-dependent kinase-4 activation. Cell 79: 487-496.

Kishi, H., Bao, J., Kohama, K. (2000) Inhibitory effects of ML-9, wortmannin, and Y-27632 on the chemotaxis of vascular smooth muscle cells in response to platelet-derived growth factor-BB. J. Biochem. (Tokyo) 128(5): 719-22.

Lerner, E.C., Qian, Y., Hamilton, A.D. and Sebti, S.M. (1995) Disruption of oncogenic K-Ras4B processing and signaling by a potent geranylgeranyltransferase I inhibitor. J. Biol. Chem. 270: 26770-26773.

Luo, Y., Marx, S.O., Kiyokawa, H., Koff, A., Massague, J., and Marks, A.R. (1996) Rapamycin resistance tied to defective regulation of $p27^{kipl}$. Mol. Cell. Biol. 16: 6744-6751.

Marx, S.O., Jayaraman, T., Go, L.O. and Marks, A.R. (1995) Rapamycin-FKBP inhibits cell cycle regulators of proliferation in vascular smooth muscle cells. Circ Res 76: 412-417.

Marx, S.O. and Marks, A.R. (2001) Bench to bedside: The development of rapamycin and its application to stent restenosis. Circulation 104: 852-855.

Ménétrey, J., Flatau, G., Stura, E.A., Charbonnier, J.B., Gas, F., Teulon, J.M., Le Du, M.H., Boquet, P. and Menez, A. (2002) NAD binding induces conformational changes in Rho ADP-ribosylating *Clostridium botulinum* C3 exoenzyme. J. Biol. Chem. 277: 30950-30957.

Negoro, N., Hoshiga, M., Seto, M., Kohbayashi, E., Ii, M., Fukui, R., Shibata, N., Nakakoji, T., Nishiguchi, F., Sasaki, Y., Ishihara, T. and Ohsawa, N. (1999) The kinase inhibitor fasudil (HA-1077) reduces intimal hyperplasia through inhibiting migration and enhancing cell loss of vascular smooth muscle cells. Biochem. Biophys. Res. Commun. 262: 211-215.

Nemoto, Y., Namba, T., Kozaki, S. and Narymiya, S. (1991) Clostridium botulinum C3 ADP-ribosyltransferase gene. Cloning, sequencing, and expression of a functional protein in *Escherichia coli*. J. Biol. Chem. 266: 19312-19319.

Nourse, J., Firpo, E., Flanagan, W.M., Coats, S., Polyak, K., Lee, M., Massague, J., Crabtree G., and Roberts, J.M. (1994) Interleukin-2-mediated elimination of the p27kip1 cyclin-dependent kinase inhibitor prevented by rapamycin. Nature (London) 372: 570-573.

Park, J., Ryu, J., Kim, K.-A., Lee, H.J., Bahn, J.H., Han, K., Choi, E.Y., Lee, K.S., Kwon, H.Y. and Choi, S.Y. (2002) Mutational analysis of a human immunodeficiency virus type 1 Tat protein transduction domain which is required for delivery of an exogenous protein into mammalian cells. J. of General Virology 83: 1173-1181.

Poon, M., Marx, S.O., Gallo, R., Badimon, J.J., Taubman, M.B. and Marks, A.R. (1996) Rapamycin inhibits vascular smooth muscle cell migration. J. Clin. Invest. 98: 2277-2283.

Popoff, M.R., Boquet, P., Gill, D.M. and Eklund, M.W. (1990) DNA sequence of exoenzyme C3, an ADP-ribosyltransferase encoded by *Clostridium botulinum* C and D phages. Nucl. Acids Res. 18: 1292.

Popoff, M.R., Hauser, D., Boquet, P., Eklund, M.W. and Gill, D.M. (1991) Characterization of the C3 gene of *Clostridium botulinum* types C and D and its expression in *Escherichia coli*. Infect. Immun. 59: 3673-3679.

Rensing, B.J., Vos, J., Smits, P.C., Foley, D.P., van den Brand, M.J. B.M., van der Giessen, W.J., de Feijter, P.J. and Serruys, P.W. (2001) Coronary restenosis elimination with a sirolimus eluting stent; first European human experience with 6-month angiographic and intravascular ultrasonic follow-up. European Heart Journal 22: 2125-2130.

Schwartz, R.S., Edelman, E.R., Carter, A., Chronos, N., Rogers, C., Robinson, K.A., Waksman, R., Weinberger, J., Wilensky, R.L., Jensen, D.N., Zuckerman, B.D. and Virmani, R. (2002) Drug-eluting stents in preclinical studies: recommended evaluation from a concensus group. Circulation 106: 1867-1873.

Schwartz, S.M. (1997) Smooth muscle migration in atherosclerosis and restenosis. J. Clin. Invest. 100: S87-89.

Seasholtz, T.M., Majumdar, M., Kaplan, D.D. and Brown, J.H. (1999) Rho and Rho kinase mediate thrombin-stimulated vascular smooth muscle cell DNA synthesis and migration. Circ. Res. 84: 1186-1193.

Sousa, J.E., Costa, M.A., Abizaid, A., Abizaid, A.S., Feres, F., Pinto, I.M.F. et al. (2000) Lack of neointimal proliferation after implantation of sirolimus-coated stents in human coronary arteries. A quantitative coronary angiography and three-dimensional intravascular ultrasound study. Circulation 102: r54-r57.

Sousa, J.E, Costa, M.A., Abizaid, A.C. Rensing, B.J., Abizaid, A.S. et al. (2001) Sustained supression of neointimal proliferation by sirolimus-eluting stents: one-year angiographic and intravascular untrasound follow-up. Circulation 104: 2007-2011.

Sun, J., Marx, S.O., Chen, H-J., Poon, M., Marks, A.R. and Rabbani, L.E. (2001) Role for p27 (Kipl) in vascular smooth muscle cell migration. Circulation 103: 2967-2972.

Wender, P.A., Mitchell, D.J., Pattabiraman, K., Pelkey, E.T., Steinman, L. and Rothbard, J.B. (2000) The design, synthesis and evaluation of molecules that enable or enhance cellular uptake: peptoid molecular transporters. Proc. Natl. Acad. Sci. (USA) 97: 13003-13008.

Winton, M.J., Dubreuil, C.I., Lasko, D., Leclerc, N. and McKerracher, L. (2002) Characterization of new cell permeable C3-like proteins that inactivate Rho and stimulate neurite outgrowth on inhibitory substrates. J. Biol. Chem. 277: 32820-32829.

International Search Report issued Aug. 24, 2005 in connection with PCT International Application No. PCT/US02/41005 on behalf of the Trustees of Columbia University in the City of New York.

C3 EXOENZYME-COATED STENTS AND USES THEREOF FOR TREATING AND PREVENTING RESTENOSIS

This application is a continuation of U.S. Ser. No. 10/326,936, filed Dec. 20, 2002, now U.S. Pat. No. 7,364,586 and claims the benefit of U.S. Provisional Application No. 60/343,030, filed Dec. 21, 2001, the contents of all of which are incorporated by reference in their entirety into this application.

Throughout this application, various publications are referenced in parentheses by author and year. Full citations for these references may be found at the end of the specification immediately preceding the claims. The disclosures of these publications in their entireties are hereby incorporated by reference into this application to more fully describe the state of the art to which this invention pertains.

BACKGROUND OF THE INVENTION

Coronary artery disease, the leading cause of mortality and morbidity in the developed world, is widely treated by implantation of stents in the coronary artery. It is estimated that more than 500,000 Americans and 1,000,000 patients internationally undergo dilation of the coronary arteries by balloon angioplasty and/or stent implantation. However, a major limitation of this revascularization procedure is the high incidence (up to 40-60%; Marx and Marks, 2001; Rensing et al., 2001) of restenosis, the recurrence of constriction of the artery following apparently successful efforts to dilate it, which often occurs within 6 months of the procedure.

Because smooth muscle cell (SMC) proliferation has been strongly implicated in the etiology of in-stent restenosis, many strategies currently being investigated to prevent coronary artery stent restenosis involve coating stents with drugs that inhibit SMC proliferation. The most promising drug evaluated to date for coating stents is rapamycin (sirolimus), an antibiotic that inhibits cell migration and proliferation (Marx and Marks, 2001; Rensing et al., 2001; Sousa et al. 2001). Recent animal and human clinical studies have shown that rapamycin-coated stents are safe and effective in reducing restenosis by more than 90%. Moreover, the luminal diameter of stented coronary arteries actually increased during follow-up in patients with rapamycin-coated stents.

Notwithstanding its early dramatic clinical success in preventing stent restenosis, rapamycin is a first-generation drug and new drugs showing similar or better efficacy with no side effects need to be developed. It has already been demonstrated that prolonged exposure of smooth muscle cells to rapamycin results in the development of resistance to the drug (Luo et al., 1996), suggesting that some patients with implanted rapamycin-coated stents might become resistant to the action of rapamycin and consequently develop restenosis.

Vascular SMC migration is believed to play a central role in the pathogenesis of many vascular diseases, including restenosis after both percutaneous transluminal angioplasty (PTCA) and coronary stenting (Schwartz, 1997). In normal blood vessels, the majority of SMCs reside in the media or middle coat of the vessel, where they are quiescent and possess a "contractile" phenotype, characterized by an abundance of actin- and myosin-containing filaments. In diseased states, however, SMCs migrate from the media to the intima or inner coat of the blood vessel.

Rapamycin, a macrolide Lactone, inhibits SMC proliferation both in vitro and in vivo by blocking cell cycle progression at the transition between the first gap (G1) and DNA synthesis (S) phases (Cao et a., 1995; Gallo et al., 1999; Gregory et al., 1993; Marx et al., 1995). The inhibition of cellular proliferation is associated with a marked reduction in cell cycle-dependent kinase activity and in retinoblastoma protein phosphorylation in vitro (Marx et al., 1995) and in vivo (Gallo et al., 1999). Down-regulation of the cyclin-dependent kinase inhibitor (CDKI), $p27^{kip1}$, by mitogens is blocked by rapamycin (Kato et al., 1994; Nourse et al., 1994).

In $p27^{kip1}$ (−/−) knockout mice, relative rapamycin resistance was demonstrated, and rapamycin-resistant myogenic cells expressed constitutively low levels of $p27^{kip1}$ that were not increased with serum withdrawal or addition of rapamycin (Luo et al., 1996).

Rapamycin has been shown to inhibit SMC migration in rats, pigs and humans (Poon et al., 1996). It also has potent inhibitory effects on SMC migration in wild type and p27 (+/−) mice, but not in p27 (−/−) knockout mice, indicating that the CDKI, $p27^{kip1}$, plays a critical role in rapamycin's anti-migratory properties and in the signaling pathway(s) that regulates SMC migration (Sun et al., 2001).

SUMMARY OF THE INVENTION

This invention provides a first stent for implantation in a blood vessel or other tissue, wherein the stent is coated with or contains C3 exoenzyme.

This invention also provides a second stent for implantation in a blood vessel or other tissue, wherein the spent is coated with or contains a chimeric C3 exoenzyme comprising C3 exoenzyme and a moiety that facilitates cellular uptake of the chimeric C3 exoenzyme.

This invention further provides a third stent for implantation in a blood vessel or other tissue, wherein the stent is coated with or contains an inhibitor of RhoA.

This invention further provides a method for treating restenosis in a subject which comprises implanting one of the instant stents in an afflicted blood vessel in the subject, thereby treating the subject.

Finally, this invention provides a method for inhibiting the onset of restenosis in a subject at risk for becoming afflicted therewith which comprises implanting any of the instant stents in the subject's blood vessel in which there is a risk for the onset of restenosis, thereby inhibiting the onset of restenosis in the subject.

BRIEF DESCRIPTION OF THE FIGURES

Rapamycin and C3 exoenzyme inhibit SMC migration through $p27^{kip1}$-dependent and -independent pathways. Growth factor receptor activation by mitogens/nutrients activates PI3-kinase, which indirectly (dashed lines) stimulates mTOR, $p70^{s6k}$ and RhoA. Rapamycin (RAPA)-FKBP12 inhibits TOR-mediated activation/phosphorylation of protein translation modulators ($p70^{s6k}$) and prevents mitogen-induced down-regulation of $p7^{kip1}$ through an unknown mechanism (lines with bars indicate inhibitory effects; arrows indicate stimulatory effects). Rapamycin inhibits SMC migration through both $p27^{kip1}$-dependent and -independent mechanisms. C3 exoenzyme, which specifically ADP ribosylates and inhibits RhoA, inhibits SMC migration through $p27^{kip1}$-dependent and -independent (cytoskeleton effects) pathways (Sun et al., 2001).

DETAILED DESCRIPTION OF THE INVENTION

Figure 1:
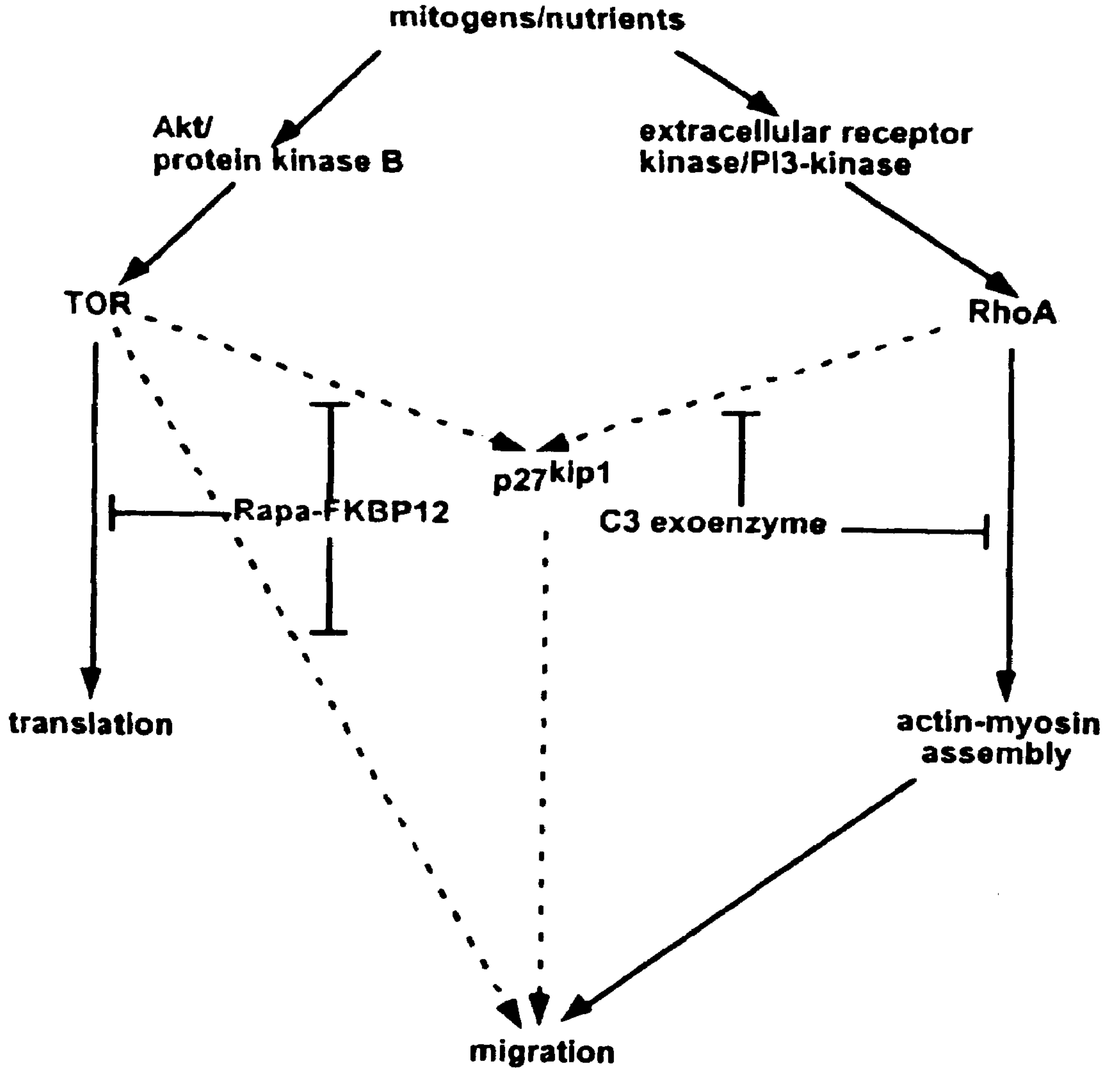

This invention provides a first stent for implantation in a blood vessel or other tissue, wherein the stent is coated with or contains C3 exoenzyme. Preferably, the C3 exoenzyme is botulinum toxin C3 exoenzyme.

This invention also provides a second stent for implantation in a blood vessel or other tissue, wherein the stent is coated with or contains a chimeric C3 exoenzyme comprising C3 exoenzyme and a moiety that facilitates cellular uptake of the chimeric C3 exoenzyme. Preferably, the chimeric C3 exoenzyme comprises botulinum toxin C3 exoenzyme.

Amino acid sequences of C3 are known, and are set forth in, for example, GenBank ID Nos. 747707, 505281, 296787 and 144737 (see, e.g., Popoff et al., 1990; Popoff et al., 1991; and Nemoto et al., 1991). The conformation of C3 exoenzyme has also been studied (Menetrey et al., 2002).

C3 exoenzyme enters cells passively with prolonged exposure (e.g., 24-49 hours) which would be afforded with a formulation that elutes off from stents over days as has been developed for rapamycin. Different formulations can provide different rates of release of the drugs from the stent.

In the second stent, the moiety that facilitates cellular uptake can be any moiety, such as a polypeptide. Such polypeptides include, without limitation, regions of other toxins that are rapidly taken up into cells, e.g., the B-subunit of diphtheria toxin (Boquet et al., 1995) and the bacterial toxin, C2 (Barth et al., 1998), as well as transit peptide sequences attached to C3 exoenzyme that facilitate protein transport across the cell membrane (see, e.g., Winton et al., 2002). Specific examples of polypeptide moieties include polylysine (e.g., KKKKKKKK), polyarginine (e.g., RRRRRRRRR) and HIV-1 Tat (Park et al., 2002). Further examples of peptides which can facilitate transport into cells include a 16 amino acid peptide-cholesterol conjugate derived from the Antennapedia homeodomain (Brugidou et al., 1995); Tatderived peptide transport molecules (U.S. Pat. Nos. 6,316,003 and 5,804,604); peptide transport polymers comprising a guanidino or amidino side chain moiety (U.S. Pat. Nos. 6,306,993 and 6,495,663); and a polyguanidine peptoid molecular transporter (Wender et al., 2000).

In one embodiment, the uptake-facilitating moiety, such as a transit peptide, is annexed to the C-terminus of C3 exoenzyme, and in another embodiment, it is annexed to the N-terminus of C3 exoenzyme. In another embodiment, such moiety increases or decreases the rate of release from the stent and/or the rate of cellular uptake.

This invention further provides a third stent for implantation in a blood vessel or other tissue, wherein the stent is coated with or contains an inhibitor of RhoA. In one embodiment of the third stent, the inhibitor of RhoA is an HMG CoA reductase inhibitor. In another embodiment, the inhibitor is a statin such as lovastatin, simvastatin, pravastatin, fluvastatin, atorvastatin, or cerivastatin. In a further embodiment, the inhibitor of RhoA is a geranylgeranyl transferase inhibitor, GGTI-298 (Lerner et al. 1995), C3 exoenzyme or a chimeric C3 exoenzyme. In one embodiment, the inhibitor inhibits prenylation of RhoA, thereby inhibiting its function. This invention still further provides a stent for implantation in a blood vessel or other tissue, wherein the stent is coated with or contains a RhoA kinase inhibitor such as Y-27632 (Seasholz et al., 1999; Kishi et al., 2000) or fasudil (Negoro et al., 1999).

Although the instant stents are preferably for use in blood vessels, they can also be used in other tissues such as those forming bodily organs or those forming a cavity, orifice or duct, in which restenosis can occur. Causes of such restenosis include, for example, organ transplantation.

The instant stents can also be coated with or contain rapamycin, taxol or actinomycin-D. In one embodiment, the instant stents are also coated with or contain two or more of rapamycin, taxol and actinomycin-D. In addition to the above-identified agents, the instant stents can also or alternatively be coated with or contain one or more bioactive agents selected from the group consisting of thrombin inhibitors, antithrombogenic agents, thrombolytic agents, fibrinolytic agents, vasospasm inhibitors, calcium channel blockers, vasodilators, antihypertensive agents, antimicrobial agents, antibiotics, inhibitors of surface glycoprotein receptors, antiplatelet agents, antimitotics, microtubule inhibitors, antisecretory agents, actin inhibitors, remodeling inhibitors, antisense nucleotides, antimetabolites, antiproliferatives, anticancer chemotherapeutic agents, anti-inflammatory steroid or non-steroidal antiinflammatory agents, immunosuppressive agents, growth hormone antagonists, growth factors, dopamine agonists, radiotherapeutic agents, peptides, proteins, enzymes, extracellular matrix components, free radical scavengers, chelators, antioxidants, antipolymerases, antiviral agents, photodynamic therapy agents, and gene therapy agents.

As used herein, a stent "coated with or containing" a medicinal agent means a stent having the agent either affixed to its surface or contained within it, so as to permit release of the agent from the stent and, hence, delivery of the agent to tissue in proximity with the stent. Methods for preparing stents (both biodegradable and non-biodegradable) for delivering medicinal agents are well known (see, e.g., U.S. Pat. Nos. 5,163,952, 5,304,121, 6,391,052, 6,387,124, 6,379,382, and 6,358,556).

This invention further provides a method for treating restenosis in a subject which comprises implanting one of the instant stents in an afflicted blood vessel in the subject, thereby treating the subject.

In one embodiment of this method, the restenosis occurs after angioplasty. In another embodiment, the restenosis occurs after vascular stent placement. The blood vessel is preferably a coronary artery, and can also be, for example, a peripheral artery or a cerebral artery. Also, in the preferred embodiment, the subject is a human.

Finally, this invention provide a method for inhibiting the onset of restenosis in a subject at risk for becoming afflicted therewith which comprises implanting one of the instant stents in the subject's blood vessel in which there is a risk for the onset of restenosis, thereby inhibiting the onset of restenosis in the subject.

In one embodiment of this method, the subject is at risk for becoming afflicted with restenosis due to angioplasty. In another embodiment, the subject is at risk for becoming afflicted with restenosis due to vascular stent placement. The blood vessel is preferably a coronary artery, and can also be, for example, a peripheral artery or a cerebral artery. Also, in the preferred embodiment, the subject is a human.

The following Experimental Details are set forth to aid in an understanding of the invention and are not intended, and should not be construed, to limit in any way the invention set forth in the claims which follow thereafter.

Experimental Details

C3 exoenzyme has been demonstrated to inhibit thrombin-mediated, vascular SMC proliferation and migration (Seasholtz et al., 1999). Similar to rapamycin, C3 exoenzyme inhibits vascular SMC migration in wild type and in p27 null mice, indicating that C3 exoenzyme acts via both p27-dependent and p27-independent pathways (Sun et al., 2001; see FIG. 1). C3 exoenzyme inhibits vascular SMC migration and proliferation in part by inhibiting RhoA which is involved in regulating p27 degradation. Thus, like rapamycin, C3 exoenzyme increases p27 levels, suggesting that C3 exoenzyme may inhibit stent restenosis by mechanisms similar to those of rapamycin.

Experiment 1

Expression and Purification of C3 Exoenzyme

C3 exoenzyme was prepared as previously described (Dillon and Feig, 1995). Competent cells of *Escherichia coli* strain BL21 were transformed with a vector containing a cDNA encoding a glutathione-S-transferase (GST)-C3 exoenzyme fusion protein. Transformed cells were grown to logarithmic phase, and expression of the fusion protein was induced with 200 μM isopropylthiogalactoside (IPTG) at 32° C. for 3 hours. Cell lysates were prepared and incubated with GST-Sepharose beads for 1 hour at 4° C. The beads were washed and incubated overnight at 4° C. with 3 units/ml thrombin (for cleavage of the C3 exoenzyme from the GST fusion protein), which was then removed by incubating the supernatant with antithrombin-Sepharose beads for 1 hour at 4° C. The supernatant was concentrated with a Centricon-10 (Amicon Inc, Beverly, Mass.). Protein concentration was determined by Bradford assay and the supernatant was aliquoted and frozen in liquid nitrogen. Samples were electrophoresed on a SDS-polyacrylamide gel and stained with Coomassie blue to confirm correct expression of the GST fusion protein and cleavage/purification of C3 exoenzyme before use (Seasholtz et al., 1999).

C3 exoenzyme is also commercially available (Biomol Research Laboratories, List Biological Laboratories), and vascular stents are commercially available (Cordis Co., Warren, N.J.). Stent implantation procedures are well known in the art (see, e.g., Sousa et al., 2001).

Experiment 2

Testing Effects of C3-Exoenzyme-Coated Stents In Vivo

C-3 exoenzyme, like rapamycin, inhibits vascular SMC migration in vitro. To confirm the effects demonstrated in non-cellular systems, the biological effects of stents coated with the active compound are investigated in vivo by implanting stents into animal models and monitoring the occurrence of restenosis after a period of time in the animal. Such tests confirm the utility of the methods of the invention for use in mammals, are useful for obtaining data on proper dosing of the drugs, and fulfill the mandate of the U.S. Food and Drug Administration for animal testing prior to use in human subjects. Specific guidelines outlining the required tests have recently been published (Schwartz et al., 2002). Testing of the C3 exoenzyme-coated stents is carried out in pigs which are commonly used for stent evaluation because of their anatomical (number and size of coronary arteries) and physiological similarity (blood clotting system) to humans. The model described here is the same previously used to test intra-coronary stents and drugs to prevent in-stent restenosis.

Juvenile, mongrel pigs of either sex, weighing 40-50 kg and in excellent health, are used in the study. A 10-20% morality is typical for studies of this type in pigs which are prone to ventricular fibrillation (VF) during manipulations of the coronary arteries, particularly if in-stent restenosis occurs. Therefore, bretylium is infused to reduce the risk of VF and the animals are subjected to continuous ECG monitoring during the procedure. If VF does occur, it is treated with DC shock. The occurrence of VF after completion of the surgical procedure when the pigs are not being monitored will result in loss of the affected pigs.

This study incorporates two different formulations of C3 exoenzyme (C3 exoenzyme-1 and -2) used on stents over periods of either 1 or 3 months:

stent+C3-1 for 1 month (n=4);
stent+C3-2 for 1 month (n=4);
stent+C3-1 for 3 months (n=4); and
stent+C3-2 for 3 months (n=4), where n is the number of pigs tested. Therefore, stents are inserted in 20 pigs which, allowing for up to 20% mortality, ensures the survival of at least 16 pigs which is the minimum number required for this preliminary study.

Experiment 3

Surgical Procedure Used to Test Efficacy of Coated Stunts In Vivo

1. One day prior to the procedure, the animals are administered aspirin (325 mg/d PO) and ticlopidine (250 mg/d), to be continued daily until the animals are euthanized.
2. Ketamin (35 mg/kg) and glycopyrrolate (0.01 mg/kg) are administered intra-muscularly as premedication.
3. Intubation and placement of a venous line are performed.
4. The animals are anesthetized with inhaled isoflurane/oxygen.
5. The right femoral groin area is shaved and sterilized.
6. Cut-down to the right femoral artery or left carotid artery is carried out, followed by arteriotomy and insertion of an 8F introducer.
7. An indwelling subclavian catheter is inserted to withdraw blood samples.
8. For heparinization, a 10,000 U IV bolus is used, and the dosage continued at 5000 U per hour.
9. Bretylium (5 mg/kg IV bolus) is administered and then infusion continued at 1 mg/min.
10. An 8F hockeystick coronary guiding catheter will be passed retrograde over a 0.038" guide wire to the aortic root and the left coronary artery will be engaged.
11. Intracoronary nitroglycerin (200 mcg) is administered.
11. Angiographic assessment of the left coronary artery is performed (by injection of the radiocontrast agent, 29% diatrizolate meglumine, during fluoroscopic visualization).
13. The angioplasty guide wire (High Torque Floppy) will be advanced into the LAD, and balloon angioplasty of the LAD will be performed (three 30 second inflations at 8 ATM). Overstretch injury will be achieved using a balloon with a diameter 30% greater than the baseline arterial diameter.
14. After balloon removal, a 3.0-3.5 mm stent with coating appropriate for the experimental group will be implanted.
15. The angioplasty and stent procedures (steps 14-15) will be repeated for the LCX artery.
16. The hardware will be removed, the artery ligated, and the cut-down site closed in three layers in a standard manner.
17. Animals are then monitored for local bleeding and adequacy of limb perfusion in an intensive care unit for 24 hours.
18. Two doses of cefazoline (25 mg/kg q 12 h) are administered after stent implantation.
19. Blood samples (10 ml each) are withdrawn at times zero, 48 hours, 3 days, 1 week, 2 weeks, 3 weeks and 4 weeks.
20. The animals are euthanized according to the AVMA Guidelines for Euthanasia (e.g., IV bolus injection of a cocktail of pentobarbital sodium, isopropyl alcohol, propylene glycol, and edetate sodium). Half of the animals are euthanized at 28 days and the remaining half at 90 days post-procedure.

The pig hearts are removed post-mortem and the coronary arteries fixed with formalin. Histological evaluation for in-stent restenosis is then performed.

All materials used during the initial implantation are provided in a sterilized state with appropriate labeling and documentation. All catheters and implants (stents) are used in single animals only. Basic surgical equipment used for cut-down is sterilized by the animal facility between uses. The surgical site is prepared and maintained in an aseptic condition throughout the procedure by shaving the right femoral groin or right neck, sterilizing the site by local application of polidine and alcohol (70%), and covering non-sterile areas with sterile drapers.

Experiment 4

Cell Migration Assay

This assay is more formally termed a "Chemotaxis Assay" since it measures the number of cells that move through a porous membrane toward a chemoattractant (e.g., a chemical or growth factor) in a given period of time. Nevertheless, it may still be referred to as a "migration assay."

Primary cells and cell culture media are obtained from Clonetics (Walkersville, Md.) and are grown at 37° C. with 5% $CO_2$. Primary human coronary artery smooth muscle cells (HCASMC) are used at passage number ≦10. They are grown in smooth muscle cell basal medium (modified MCDB 131), with the addition of 5% fetal bovine serum (FBS), 0.5 μg/ml human epidermal growth factor (hEGF), 5 mg/ml insulin, 1.0 μg/ml human fibroblast growth factor, 50 mg/ml gentamycin and 50 μg/ml amphoteracin B.

Primary human coronary vascular endothelial cells (HCVEC) are used at passage number ≦10. They are grown in endothelial cell basal medium (modified MCDB 131), with the addition of 5% FBS, 10 μg/ml hEGF, 1.0 mg/mL hydrocortisone, 3 mg/ml bovine brain extract, 50 mg/ml gentamycin and 50 μg/ml amphoteracin B.

Cells are removed from flasks by brief exposure to trypsin-EDTA (Invitrogen), followed by inactivation in complete medium, centrifugation for 5 min. at 2,000 rpm, and resuspension in basal medium at a concentration of $2\times10^5$ cells per 250 μl. Cells are pipetted into the upper chamber of BD Falcon FluoroBlok™ 24-well insert plates (modified Boyden chambers; BD Biosciences, Bilerica, Mass.), containing fibronectin-coated filters with either 3 μm or 8 μm pores. The lower chamber contains basal medium with the addition of chemoattractants such as serum or growth factors. For HCASMC, either FBS or human platelet-derived growth factor BB (hPDGF-BB) is used. For HCVEC, either FBS or human vascular endothelial growth factor (hVEGF) is used.

After cells are added to the top chamber, along with various concentrations of drugs that are being tested for the inhibition of migration, the bottom chamber is filled with 0.75 ml of basal medium containing chemoattractant. The plates are then incubated for either 6 hours or 22 hours at 37° C.

At the end of the incubation period, liquid in the top chamber of each well is aspirated, and the top half of he plate (containing the 24 upper chambers to which the permeable filters are fused) is lifted off, and excess liquid is shaken into a sink. The top half of the plate is then placed into a fresh 24-well plate, each well of which contains 0.75 ml Calcein AM solution (4 μg/ml; Molecular Probes, Eugene, Oreg.). The complete assembly is then incubated at 37° C. for 90 min., during which time the Calcein AM stains the cells that remained attached to the filter. The stained plate is then placed in a Victor II plate reader (PerkinElmer, Boston, Mass.) that is programmed to read from the bottom, with excitation at 485 nm, emission at 535 nm, and a 0.1 second read time. Since the filter through which the cells have migrated has a dark, opaque color, the excitation or emission light does not penetrate the filter. Thus, only cells that have migrated through to the underside of the filter will be detected by the fluorescence plate reader.

Data, recorded in arbitrary fluorescence units and analyzed using Prism v 3.02 (Graphpad Software), are typically expressed as percent migration.

Experiment 5

Proliferation Assay

This assay measures the number of live cells in a tissue culture dish or well. It does so by monitoring the color change of the tetrazolium salt, WST-1, which is modified by a mitochondrial enzyme involved in respiration. This enzyme is only active in living cells. The assay is similar to others such as MTT or MTS, which measure the same activity using different tetrazolium chromophores.

Primary cells and cell culture media are obtained from Clonetics (Walkersville, Md.) and are grown at 37° C. in a humidified incubator containing 5% $CO_2$. Primary human coronary artery smooth muscle cells (HCASMC) are used at passage number ≦10. They are grown in smooth muscle cell basal medium (modified MCDB 131), with the addition of: 5% fetal bovine serum (FBS); 0.5 μg/ml human epidermal growth factor (hEGF); 5 mg/ml insulin; 1.0 μg/ml human fibroblast growth factor; 50 mg/ml gentamycin; and 50 μg/ml amphoteracin B.

Primary human coronary vascular endothelial cells (HCVEC) are used at passage number ≦10. They are grown in endothelial cell basal medium (modified MCDB 131), with the addition of: 5% FBS; 10 μg/ml hEGF; 1.0 mg/ml hydrocortisone; 3 mg/ml bovine brain extract; 50 mg/ml gentamycin; and 50 μg/ml amphoteracin B.

Cells are removed from flasks by brief exposure to trypsin-EDTA (Invitrogen), followed by inactivation in complete medium, centrifugation for 5' at 2,000 rpm, and re-suspension in complete medium. Cells are counted using a hemocytometer and plated into 96-well tissue culture plates at $5\times10^3$ cells/well in 50 μl Test compounds ire dissolved either in DMSO or PBS, such that the final concentration of DMSO in the assay is 0.2%. Compounds are prepared at twice the final assay concentration in complete medium, and 50 μl are added to each well. The plates are then incubated for 2-7 days at 37° C.

At the end of the incubation period, 10 μl WST-1 reagent (Roche Molecular Biochemicals, Indianapolis, Ind.) are added to each well, followed by incubation at 37° C. for 90 minutes. During this time, the color change in the WST-1 reagent correlates with the number of live cells in each well. At the end of the incubation period, plates containing live cells can be analyzed immediately, or 15 μl of 10% sodium dodecyl sulfate (SDS) can be added to each well, thus lysing the cells and preserving the assay for later analysis. Plates are analyzed (0.1 second/well) for absorbance at 450 nm in a Victor II plate reader (PerkinElmer, Boston, Mass.).

Data are expressed as arbitrary absorbance units (correlating with the number of live cells) and analyzed using Prism v 3.02 (Graphpad Software).

REFERENCES

Barth, H., Hofmann, F., Olenik, C., Just, I. and Aktories, K. (1998) The N-terminal part of the enzyme component (C2I) of the binary *Clostridium botulinum* C2 toxin interacts with the binding component C2II and functions as a carrier system for a Rho ADP-ribosylating C3-Like fusion toxin. Infect. Immun. 66: 1364-1369.

Boquet, P., Popoff, M. R., Giry, M., Lemichez, E. and Bergez-Aullo, P. (1995) Inhibition of p21 Rho in intact cells by C3 diphtheria toxin chimera proteins. Methods Enzymol. 256: 297-306.

Brugidou, J. et al. (1995) Biochem. Biophys. Res. Comm. 214(2): 685-693.

Cao, W., Mohacsi, P., Shorthouse, R., Pratt, R., and Morris, R. (1995) Effects of rapamycin on growth factor-stimulated vascular smooth muscle cell DNA synthesis: inhibition of basic fibroblast growth factor and platelet-derived growth factor action and antagonism of rapamycin by FK506. Transplantation 59: 390-395.

Dillon, S. T., and Feig, L. A. (1995) Purification and assay of recombinant C3 transferase. Methods in Enzymology 256: 174-184.

Gallo, R., Padurean, A., Jayaraman, T., Marx, S. O., Roque, M., Adelman, S., Chesebro, J., Fallon, J., Fuster, V., Marks, A. R., and Badimon, J. J. (1999) Inhibition of intimal thickening after balloon angioplasty in porcine coronary arteries by targeting regulators of the cell cycle. Circulation 99: 2164-2170.

Gregory, C., Huie, P., Billingham, M., and Morris, P. (1993) Rapamycin inhibits arterial intimal thickening caused by both alloimmune and mechanical injury. Transplantation 55: 1409-1418.

Kato, J. M., Matsuoka, M., Polyak, K., Massague, J., and Sherr, C. J. (1994) Cyclic AMP-induced G1 phase arrest mediated by an inhibitor ($p27^{kip1}$) of cyclin-dependent kinase-4 activation. Cell 79: 487-496.

Kishi, H., Bao, J., Kohama, K. (2000) Inhibitory effects of ML-9, wortmannin, and Y-27632 on the chemotaxis of vascular smooth muscle cells in response to platelet-derived growth factor-BB. J. Biochem. (Tokyo) November: 128(5): 719-22.

Lerner, E. C., Qian, Y., Hamilton, A. D. and Sebti, S. M. (1995) Disruption of oncogenic K-Ras4B processing and signaling by a potent geranylgeranyltransferase I inhibitor. J. Biol. Chem. 270: 26770-26773.

Luo, Y., Marx, S. O., Kiyokawa, H., Koff, A., Massague, J., and Marks, A. R. (1996) Rapamycin resistance tied to defective regulation of $p27^{kip1}$. Mol. Cell. Biol. 16: 6744-6751.

Marx, S. O., Jayaraman, T., Go, L. O., and Marks, A. R. (1995) Rapamycin-FKBP inhibits cell cycle regulators of proliferation in vascular smooth muscle cells. Circ Res 76: 412-417.

Marx, S. O. and Marks, A. R. (2001) Bench to bedside: The development of rapamycin and its application to stent restenosis. Circulation 104: 852-855.

Menetrey, J., Flatau, G., Stura, E. A., Charbonnier, J. B., (Gas, F., Teulon, J. M., Le Du, M. H., Boquet, P. and Menez, A. (2002) NAD binding induces conformational changes in Rho ADP-ribosylating clostridium botulinum C3 exoenzyme. J. Biol. Chem. 277, 34: 30950-30957.

Negoro, N., Hoshiga, M., Seto, M., Kohbayashi, E., Ii, M., Fukui, R., Shibata, N., Nakakoji, T., Nishiguchi, F., Sasaki, Y., Ishihara, T. and Ohsawa, N. (1999) The kinase inhibitor fasudil (HA-1077) reduces intimal hyperplasia through inhibiting migration and enhancing cell loss of vascular smooth muscle cells. Biochem. Biophys. Res. Commun. 262: 211-215.

Nemoto, Y., Namba, T., Kozaki, S. & Narumiya, S. (1991) Clostridium botulinum C3 ADP-ribosyltransferase gene. Cloning, sequencing, and expression of a functional protein in *Escherichia coli*. J. Biol. Chem. 266, 29: 19312-19319.

Nourse, J., Firpo, E., Flanagan, W. M., Coats, S., Polyak, K., Lee, M., Massague, J., Crabtree, G., and Roberts, J. M. (1994) Interleukin-2-mediated elimination of the p27kip1 cyclin-dependent kinase inhibitor prevented by rapamycin. Nature (London) 372: 570-573.

Park, J., Ryu, J., Kim, K.-A., Lee, H. J., Bahn, J. H., Han, K., Choi, E. Y., Lee, K. S., Kwon, H. Y., and Choi, S. Y. (2002) Mutational analysis of a human immunodeficiency virus type 1 Tat protein transduction domain which is required for delivery of an exogenous protein into mammalian cells. J. of General Virology 83: 1173-1181.

Poon, M., Marx, S. O., Gallo, R., Badimon, J. J., Taubman, M. B., and Marks, A. R. (1996) Rapamycin inhibits vascular smooth muscle cell migration. J. Clin. Invest. 98: 2277-2283.

Popoff, M. R., Hauser, D., Boquet, P., Eklund, M. W. and Gill, D. M. (1990) Characterization of the C3 gene of *Clostridium botulinum* types C and D and its expression in *Escherichia coli*. Infect. Immun. 59, 10: 3673-3679.

Popoff, M. R., Hauser, D., Boquet, P., Eklund, M. W. and Gill, D. M. (1991) Characterization of the C3 gene of *Clostridium botulinum* types C and D and its expression in *Escherichia coli*. Infect. Immun. 59, 10: 3673-3679.

Rensing, B. J., Vos, J., Smits, P. C., Foley, D. P., van den Brand, M. J. B. M., van der Giessen, W. J., de Feijter, P. J. and Serruys, P. W. (2001) Coronary restenosis elimination with a sirolimus eluting stent; first European human experience with 6-month angiographic and intravascular ultrasonic follow-up. European Heart Journal 22: 2125-2130.

Schwartz, S. M. (1997) Smooth muscle migration in atherosclerosis and restenosis. J. Clin. Invest. 100: S87-98.

Schwartz, R. S., Edelman, E. R., Carter, A., Chronos, N., Rogers, C., Robinson, K. A., Waksman, R., Weinberger, J., Wilensky, R. L., Jensen, D. N., Zuckerman, B. D. and Virmani, R. (2002) Drug-eluting stents in preclinical Studies: recommended evaluation from a consensus group. Circulation 106: 1867-1873.

Seasholtz, T. M., Majumdar, M., Kaplan, D. D., and Brown, J. H. (1999) Rho and Rho kinase mediate thrombin-stimulated vascular smooth muscle cell DNA synthesis and migration. Circ. Res. 84: 1186-1193.

Sousa, J. E., Costa, M. A., Abizaid, A., Abizaid, A. S., Feres, F., Pinto, I. M. F. et al. (2000) Lack of neointimal proliferation after implantation of sirolimus-coated stents in human coronary arteries. A quantitative coronary angiography and three-dimensional intravascular ultrasound study. Circulation 102: r54-r57.

Sun, J., Marx, S. O., Chen, H-J., Poon, M., Marks, A. R. and Rabbani, L. E. (2001) Role for p27(Kip1) in vascular smooth muscle cell migration. Circulation 103: 2967-2972.

Wender P. A., et al. (2000) P.N.A.S. (USA) November 21; 97(24): 13003-8.

Winton, M. J., Dubreuil, C. I., Lasko, D., Leclerc, N. and McKerracher, L. (2002) Characterization of new cell permeable C3-like proteins that inactivate Rho and stimulate neurite outgrowth on inhibitory substrates. J. Biol. Chem. 277: 32820-32829.

What is claimed is:

1. A method for treating restenosis in a subject which comprises implanting an article of manufacture comprising a stent, wherein the stent is coated with or contains (i) C3 exoenzyme and rapamycin, (ii) C3 exoenzyme and paclitaxel, (iii) C3 exoenzyme and actinomycin-D, (iv) a chimeric C3 exoenzyme comprising C3 exoenzyme and polylysine, (v) a chimeric C3 exoenzyme comprising C3 exoenzyme and polyarginine, or (vi) a chimeric C3 exoenzyme comprising C3 exoenzyme and HIV-1 Tat, in an afflicted blood vessel in the subject, thereby treating the subject.

2. The method of claim 1, wherein the restenosis occurs after angioplasty.

3. The method of claim 1, wherein the restenosis occurs after vascular stent placement.

4. The method of claim 1, wherein the blood vessel is a coronary artery.

5. The method of claim 1, wherein the subject is a human.

6. The method of claim 1, wherein the C3 exoenzyme is botulinum toxin C3 exoenzyme.

7. The method of claim 1, wherein the stent coated with or containing C3 exoenzyme and rapamycin is also coated with or contains paclitaxel.

8. The method of claim 7, wherein the stent is also coated with or contains actinomycin-D.

9. The method of claim 1, wherein the stent coated with or containing C3 exoenzyme and rapamycin is also coated with or contains actinomycin-D.

10. The method of claim 1, wherein the stent coated with or containing C3 exoenzyme and paclitaxel is also coated with actinomycin-D.

11. The method of claim 1, wherein the chimeric C3 exoenzyme comprises botulinum toxin C3 exoenzyme.

12. The method of claim 1, wherein the stent coated with or containing a chimeric C3 exoenzyme comprising C3 exoenzyme and polylysine is also coated with or contains rapamycin.

13. The method of claim 1, wherein the stent coated with or containing a chimeric C3 exoenzyme comprising C3 exoenzyme and polylysine is also coated with or contains paclitaxel.

14. The method of claim 1, wherein the stent coated with or containing a chimeric C3 exoenzyme comprising C3 exoenzyme and polylysine is also coated with or contains actinomycin-D.

15. The method of claim 1, wherein the stent coated with or containing a chimeric C3 exoenzyme comprising C3 exoenzyme and polylysine is also coated with or contains rapamycin and paclitaxel.

16. The method of claim 1, wherein the stent coated with or containing a chimeric C3 exoenzyme comprising C3 exoenzyme and polylysine is also coated with or contains rapamycin and actinomycin-D.

17. The method of claim 1, wherein the stent coated with or containing a chimeric C3 exoenzyme comprising C3 exoenzyme and polylysine is also coated with or contains paclitaxel and actinomycin-D.

18. The method of claim 1, wherein the stent coated with or containing a chimeric C3 exoenzyme comprising C3 exoenzyme and polylysine is also coated with or contains rapamycin, paclitaxel and actinomycin-D.

19. The method of claim 1, wherein the stent coated with or containing a chimetic C3 exoenzyme comprising C3 exoenzyme and polyarginine is also coated with or contains rapamycin.

20. The method of claim 1, wherein the stent coated with or containing a chimetic C3 exoenzyme comprising C3 exoenzyme and polyarginine is also coated with or contains paclitaxel.

21. The method of claim 1, wherein the stent coated with or containing a chimetic C3 exoenzyme comprising C3 exoenzyme and polyarginine is also coated with or contains actinomycin-D.

22. The method of claim 1, wherein the stent coated with or containing a chimeric C3 exoenzyme comprising C3 exoenzyme and polyarginine is also coated with or contains rapamycin and paclitaxel.

23. The method of claim 1, wherein the stent coated with or containing a chimeric C3 exoenzyme comprising C3 exoenzyme and polyarginine is also coated with or contains rapamycin and actinomycin-D.

24. The method of claim 1, wherein the stent coated with or containing a chimeric C3 exoenzyme comprising C3 exoenzyme and polyarginine is also coated with or contains paclitaxel and actinomycin-D.

25. The method of claim 1, wherein the stent coated with or containing a chimeric C3 exoenzyme comprising C3 exoenzyme and polyarginine is also coated with or contains rapamycin, paclitaxel and actinomycin-D.

26. The method of claim 1, wherein the stent coated with or containing a chimeric C3 exoenzyme comprising C3 exoenzyme and HIV-1 Tat is also coated with or contains rapamycin.

27. The method of claim 1, wherein the stent coated with or containing a chimeric C3 exoenzyme comprising C3 exoenzyme and HIV-1 Tat is also coated with or contains paclitaxel.

28. The method of claim 1, wherein the stent coated with or containing a chimeric C3 exoenzyme comprising C3 exoenzyme and HIV-1 Tat is also coated with or contains actinomycin-D.

29. The method of claim 1, wherein the stent coated with or containing a chimeric C3 exoenzyme comprising C3 exoenzyme and HIV-1 Tat is also coated with or contains rapamycin and paclitaxel.

30. The method of claim 1, wherein the stent coated with or containing a chimeric C3 exoenzyme comprising C3 exoenzyme and HIV-1 Tat is also coated with or contains rapamycin and actinomycin-D.

31. The method of claim 1, wherein the stent coated with or containing a chimeric C3 exoenzyme comprising C3 exoenzyme and HIV-1 Tat is also coated with or contains paclitaxel and actinomycin-D.

32. The method of claim 1, wherein the stent coated with or containing a chimeric C3 exoenzyme comprising C3 exoenzyme and HIV-1 Tat is also coated with or contains rapamycin, paclitaxel and actinomycin-D.

33. A method for inhibiting the onset of restenosis in a subject at risk for becoming afflicted therewith which comprises implanting an article of manufacture comprising a stent, wherein the stent is coated with or contains (i) C3 exoenzyme and rapamycin, (ii) C3 exoenzyme and paclitaxel, (iii) C3 exoenzyme and actinomycin-D, (iv) a chimeric C3 exoenzyme comprising C3 exoenzyme and polylysine, (v) a chimeric C3 exoenzyme comprising C3 exoenzyme and polyarginine, or (vi) a chimeric C3 exoenzyme comprising C3 exoenzyme and HIV-1 Tat, in the subject's blood vessel, thereby inhibiting the onset of restenosis in the subject.

34. The method of claim 33, wherein the subject is at risk for becoming afflicted with restenosis due to angioplasty.

35. The method of claim 33, wherein the subject is at risk for becoming afflicted with restenosis due to vascular stent placement.

36. The method of claim 33, wherein the blood vessel is a coronary artery.

37. The method of claim 33, wherein the subject is a human.

38. The method of claim 33, wherein the C3 exoenzyme is botulinum toxin C3 exoenzyme.

39. The method of claim 33, wherein the stent coated with or containing C3 exoenzyme and rapamycin is also coated with or contains paclitaxel.

40. The method of claim 39, wherein the stent is also coated with or contains actinomycin-D.

41. The method of claim 33, wherein the stent coated with or containing C3 exoenzyme and rapamycin is also coated with or contains actinomycin-D.

42. The method of claim 33, wherein the stent coated with or containing C3 exoenzyme and paclitaxel is also coated with actinomycin-D.

43. The method of claim 33, wherein the chimeric C3 exoenzyme comprises botulinum toxin C3 exoenzyme.

44. The method of claim 33, wherein the stent coated with or containing a chimeric C3 exoenzyme comprising C3 exoenzyme and polylysine is also coated with or contains rapamycin.

45. The method of claim 33, wherein the stent coated with or containing a chimeric C3 exoenzyme comprising C3 exoenzyme and polylysine is also coated with or contains paclitaxel.

46. The method of claim 33, wherein the stent coated with or containing a chimeric C3 exoenzyme comprising C3 exoenzyme and polylysine is also coated with or contains actinomycin-D.

47. The method of claim 33, wherein the stent coated with or containing a chimeric C3 exoenzyme comprising C3 exoenzyme and polylysine is also coated with or contains rapamycin and paclitaxel.

48. The method of claim 33, wherein the stent coated with or containing a chimeric C3 exoenzyme comprising C3 exoenzyme and polylysine is also coated with or contains rapamycin and actinomycin-D.

49. The method of claim 33, wherein the stent coated with or containing a chimeric C3 exoenzyme comprising C3 exoenzyme and polylysine is also coated with or contains paclitaxel and actinomycin-D.

50. The method of claim 33, wherein the stent coated with or containing a chimeric C3 exoenzyme comprising C3 exoenzyme and polylysine is also coated with or contains rapamycin, paclitaxel and actinomycin-D.

51. The method of claim 33, wherein the stent coated with or containing a chimetic C3 exoenzyme comprising C3 exoenzyme and polyarginine is also coated with or contains rapamycin.

52. The method of claim 33, wherein the stent coated with or containing a chimetic C3 exoenzyme comprising C3 exoenzyme and polyarginine is also coated with or contains paclitaxel.

53. The method of claim 33, wherein the stent coated with or containing a chimetic C3 exoenzyme comprising C3 exoenzyme and polyarginine is also coated with or contains actinomycin-D.

54. The method of claim 33, wherein the stent coated with or containing a chimeric C3 exoenzyme comprising C3 exoenzyme and polyarginine is also coated with or contains rapamycin and paclitaxel.

55. The method of claim 33, wherein the stent coated with or containing a chimeric C3 exoenzyme comprising C3 exoenzyme and polyarginine is also coated with or contains rapamycin and actinomycin-D.

56. The method of claim 33, wherein the stent coated with or containing a chimeric C3 exoenzyme comprising C3 exoenzyme and polyarginine is also coated with or contains paclitaxel and actinomycin-D.

57. The method of claim 33, wherein the stent coated with or containing a chimeric C3 exoenzyme comprising C3 exoenzyme and polyarginine is also coated with or contains rapamycin, paclitaxel and actinomycin-D.

58. The method of claim 33, wherein the stent coated with or containing a chimeric C3 exoenzyme comprising C3 exoenzyme and HIV-1 Tat is also coated with or contains rapamycin.

59. The method of claim 33, wherein the stent coated with or containing a chimeric C3 exoenzyme comprising C3 exoenzyme and HIV-1 Tat is also coated with or contains paclitaxel.

60. The method of claim 33, wherein the stent coated with or containing a chimeric C3 exoenzyme comprising C3 exoenzyme and HIV-1 Tat is also coated with or contains actinomycin-D.

61. The method of claim 33, wherein the stent coated with or containing a chimeric C3 exoenzyme comprising C3 exoenzyme and HIV-1 Tat is also coated with or contains rapamycin and paclitaxel.

62. The method of claim 33, wherein the stent coated with or containing a chimeric C3 exoenzyme comprising C3 exoenzyme and HIV-1 Tat is also coated with or contains rapamycin and actinomycin-D.

63. The method of claim 33, wherein the stent coated with or containing a chimeric C3 exoenzyme comprising C3 exoenzyme and HIV-1 Tat is also coated with or contains paclitaxel and actinomycin-D.

64. The method of claim 33, wherein the stent coated with or containing a chimeric C3 exoenzyme comprising C3 exoenzyme and HIV-1 Tat is also coated with or contains rapamycin, paclitaxel and actinomycin-D.

* * * * *